United States Patent
Ruggiero

Patent Number: 6,123,013
Date of Patent: Sep. 26, 2000

[54] MEASUREMENT APPARATUS FOR PASTA PREPARATION

[76] Inventor: Nicola Ruggiero, Via Salgareto, 146, 47040 Montecolombo (RN), Italy

[21] Appl. No.: 09/303,590

[22] Filed: May 3, 1999

Related U.S. Application Data

[63] Continuation of application No. PCT/IB97/01389, Nov. 4, 1997.

[30] Foreign Application Priority Data

Nov. 8, 1996 [IT] Italy ............... FO96A000025

[51] Int. Cl.[7] .............. A23L 1/00; A47J 27/00; A47J 27/04; G01K 1/02; G01K 13/00

[52] U.S. Cl. .............. 99/331; 99/342; 99/344; 99/403; 73/73

[58] Field of Search ............... 99/330, 331–333, 99/403–417, 342–344, 493; 126/351, 374, 388; 73/73, 64, 69, 49, 54.22, 865.8, 587; 426/233, 465

[56] References Cited

U.S. PATENT DOCUMENTS

| | | | |
|---|---|---|---|
| 2,367,117 | 1/1945 | Gougeon | 99/342 X |
| 4,210,020 | 7/1980 | Wasik | |
| 4,741,261 | 5/1988 | DiMaria | 99/330 |
| 5,586,487 | 12/1996 | Marino | 99/403 X |
| 5,620,255 | 4/1997 | Cook, III | 99/342 |

FOREIGN PATENT DOCUMENTS 01240205  11/1993  Italy.

*Primary Examiner*—Timothy Simone
*Attorney, Agent, or Firm*—Akin, Gump, Strauss, Hauer & Feld, L.L.P.

[57] ABSTRACT

An instrument for measuring the stage of cooking of pasta in a cooking liquid including a gripper (112) immersed in the cooking liquid. The gripper includes a squeezer (12) to retain and elastically compress a sample of the pasta (30). The squeezer (12) includes a stationary contrasting element and an elastic compression element which includes an elastic with a fixed setting. The elastic compression element is movable with respect to the stationary contrasting element in a manner functionally correlated to the progressive loss of consistency of the sample of the pasta (30) as cooking proceeds. The instrument further includes an electrical circuit (34) having at least one contact (33) and a signal (37). The position of the contact (33) is correlated to a predetermined state of cooking of the pasta (30). A monitoring rod (20) is attached to the elastic compression element and emerges from the cooking container. A pivoting element is attached to the monitoring rod (20) and cooperates electrically with the at least one contact (33) to close the electrical circuit (34) in response to movement of the monitoring rod (20) as the cooking of the sample of the pasta (30) proceeds to the predetermined state of cooking of the pasta (30), thereby activating the signal (37).

10 Claims, 3 Drawing Sheets

MEASUREMENT APPARATUS FOR PASTA PREPARATION

CROSS-REFERENCE TO RELATED APPLICATION

This application is a continuation of International Application PCT/IB97/01389, filed Nov. 4, 1997, the disclosure of which is incorporated herein by reference.

BACKGROUND OF THE INVENTION

This invention concerns an instrument to measure the stage of cooking of pasta as set forth in the main claim.

The measuring instrument according to the invention is used in normal and everyday domestic, professional and industrial operations to verify the stage of cooking reached by the pasta, whatever form it may be, without the risk of burns, or of dropping pieces of pasta previously picked out for tasting, or of over-cooking due to forgetfulness—in short, avoiding all those problems well-known to everyone and ensuring a precise cooking to a desired stage which can be pre-set.

In the following description we shall speak of pasta cooked in water, however it is implicit that the invention may be used also for pasta or other food products cooked in broth, milk or other liquids.

Every time pasta is cooked, whatever the shape of the pasta (spaghetti, short pasta, macaroni, stuffed pasta etc.), it is necessary to bring water to the boil and then add the desired quantity of pasta.

To verify the stage of cooking the user usually refers to the time which is normally shown on the pasta box, and then possibly tastes the pasta from time to time so as to verify the progress of the cooking.

However, the cooking time shown on the box is not a safe and reliable parameter; it gives an approximate indication for an average cooking stage but it does not offer the possibility, except on a theoretical and approximate level, of obtaining personalised stages of cooking ("al dente", very "al dente", well cooked, etc.).

Moreover, this parameter is affected by external conditions which make it quite imprecise, such as the amount of salt in the water, the period of time for which the water stops boiling when the pasta is added, external humidity, the ratio of pasta to water and other factors.

However, everybody knows the problems which arise when the cook wants to taste a sample of the pasta to verify what stage of cooking it has reached: burnt hands, burnt tongue, dropped pieces of pasta, disagreement over the stage of cooking reached by the pasta and other problems.

Other times the cook may rely on a visual estimate of the inner part of the piece of pasta, but these estimates are necessarily subjective and approximate.

It should also be considered that there are many different types of pasta which differ in the type of wheat used and in the methods of working and preservation; this influences the time required for the pasta to cook and therefore involves other difficulties in any evaluation of the cooking stage based on empirical methods and/or strictly on time.

The applicant is not aware of any device able to provide users with a substantially automatic and precise indication of the stage of cooking reached by pasta, regardless of type, shape, state and time of preservation, which will prevent the user from suffering from those "classical" domestic accidents caused by tasting the pasta, and which will offer the possibility of selecting the desired degree of cooking in a completely objective and automatic way which is independent of personal and empirical evaluations.

IT-B-1.240.205 describes an instrument to measure the stage of cooking of pasta, consisting of an axially sliding hook-shaped cylinder and of a stationary part which constitutes the body of the instrument.

The hook is immersed into the liquid where the pasta is cooked and compresses a sample of pasta between itself and the stationary part of the instrument.

The force of compression of the hook is regulated by an inner spring with a variable setting.

When the pasta reaches a particular stage of cooking, with the relative loss of consistency, the force of compression of the hook is able to cut the sample of pasta; this cutting action causes a warning signal, either visual or audio, to be emitted.

This embodiment does not allow a continual measurement of the consistency of the pasta and therefore it does not allow to select, even during the cooking operation itself, different pre-determined degrees of cooking according to the tastes of the user.

For this purpose the applicant has designed, tested and embodied this invention.

SUMMARY OF THE INVENTION

The invention is set forth and characterised in the main claim, while the dependent claims describe variants of the idea of the main embodiment.

The purpose of the invention is to achieve an instrument to measure the stage of cooking of pasta which will be able to provide automatically, without the need for any tasting, a signal to the user that the pasta has reached the desired stage of cooking.

This measurement is carried out directly on a sample of pasta being cooked; it is therefore independent of any external conditioning factor and is not connected to parameters of time which often do not give a sufficiently precise and valid indication in whatsoever condition.

A further purpose is to provide a device which will make it possible to select a plurality of cooking stages which can be set in advance according to the tastes of the users and independent of their personal and subjective sensations.

When the pre-selected stage of cooking is reached, the instrument according to the invention gives a visual and/or audio signal to the user who is thus advised and can proceed to remove the saucepan from the heat and drain the pasta.

According to a variant, the instrument according to the invention is connected to the cooking appliance and automatically causes the gas, or more generally the heating element, to be turned off when the desired stage of cooking is reached.

According to another variant, the measuring instrument according to the invention is integrated into a basket-type equipment in order to drain the pasta directly inside the saucepan wherein it is cooked.

The measuring instrument according to the invention comprises a gripper element which, during the operational phase, is immersed into the saucepan wherein the pasta is cooked.

A sample of cooked pasta is inserted into the gripper element.

The gripper element is placed at the end of a supporting element which includes attachment means to attach it to the edge, or other desired part, of the saucepan.

The gripper element is also rigidly connected to a monitoring rod which protrudes from the saucepan and includes at the upper part a horizontally pivoting element associated with signal means.

The gripper element consists of a squeezer element, inside which the sample of pasta is inserted and clamped inside the cooking water.

The squeezer element is functionally and elastically connected, by means of spring elements, to the monitoring rod.

According to the invention, the progressive cooking of the pasta causes the gripper element to squeeze the sample of pasta which gradually loses its hardness and consistency.

Thanks to the inclusion of the elastic elements, the movement of the gripping organs of the squeezer element causes a correlated displacement of the monitoring rod which, due to this displacement, moves the pivoting element which is connected thereto.

The pivoting element is thus taken progressively into correspondence with the signal means, and when these are reached, a signal is emitted to show that the desired degree of cooking has been reached;

According to a variant, there are also selection means which allow a desired degree of cooking ("al dente", very "al dente", well cooked, etc.) to be pre-defined, and the signal means activate the pivoting element only when this degree of cooking has been reached.

According to another variant, the squeezer element cooperates with sensor means which monitor the progressive displacement as cooking advances and send an electric signal to the signal means.

BRIEF DESCRIPTION OF THE SEVERAL VIEWS OF THE DRAWINGS

The attached figures are given as a non-restrictive example and show some preferential embodiments of the invention as follows.

DETAILED DESCRIPTION OF THE INVENTION

Figure 1:
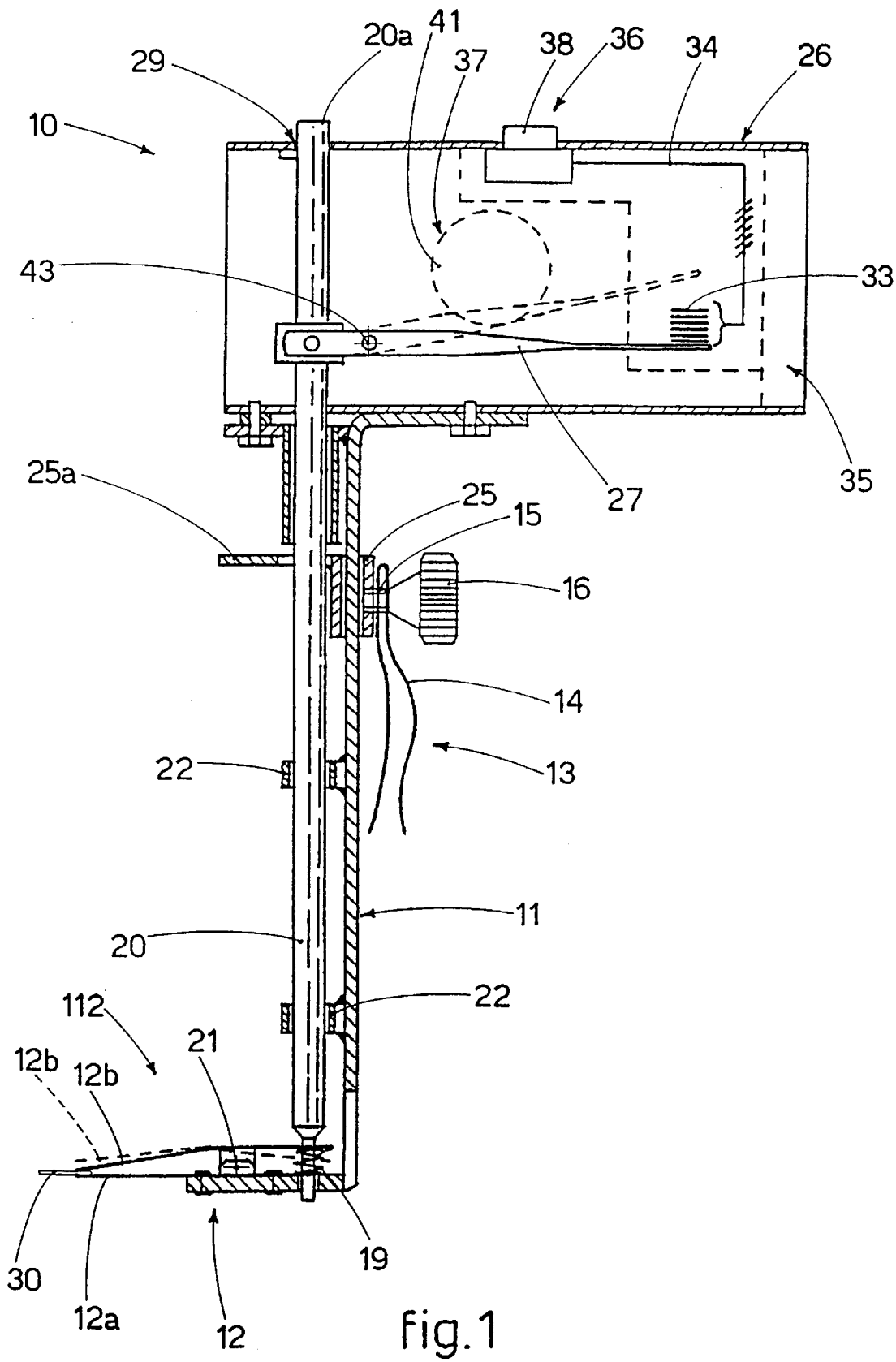
FIG. 1 shows a lengthwise cross section of a first embodiment of the invention.

With reference to the attached figures, the reference number 10 denotes generally the instrument to measure the stage of cooking reached by pasta according to the invention.

The instrument 10 is introduced inside the container or saucepan to cook the pasta or other food immersed in a cooking liquid, and comprises a supporting element 11; a gripper element 112 comprising a squeezer element 12 is associated in correspondence with the lower end of the supporting element 11.

Attachment means 13 which allow the supporting element 11 to be associated with the edge of the saucepan are constrained to the said supporting element 11.

The attachment means 13 can be moved and regulated along the supporting element 11 so as to constrain it to the edge of saucepans of different depths and for different quantities of water contained therein.

In the case of FIG. 1, the attachment means 13 comprise an elastic fin 14, shaped like an upside-down "U", which is inserted on the edge of the saucepan and on which screw-type means 15 act, the screw-type means 15 being associated at the ends with a handle 16.

The screw-type means 15 are associated with an angular profile 25, in such a way as to allow the angular profile to be clamped onto the supporting element 11 in order to clamp the elastic fin 14 in the desired position.

The forward extension 25a of the angular profile 25 constitutes the supporting element for the lid of the saucepan.

Figure 2:
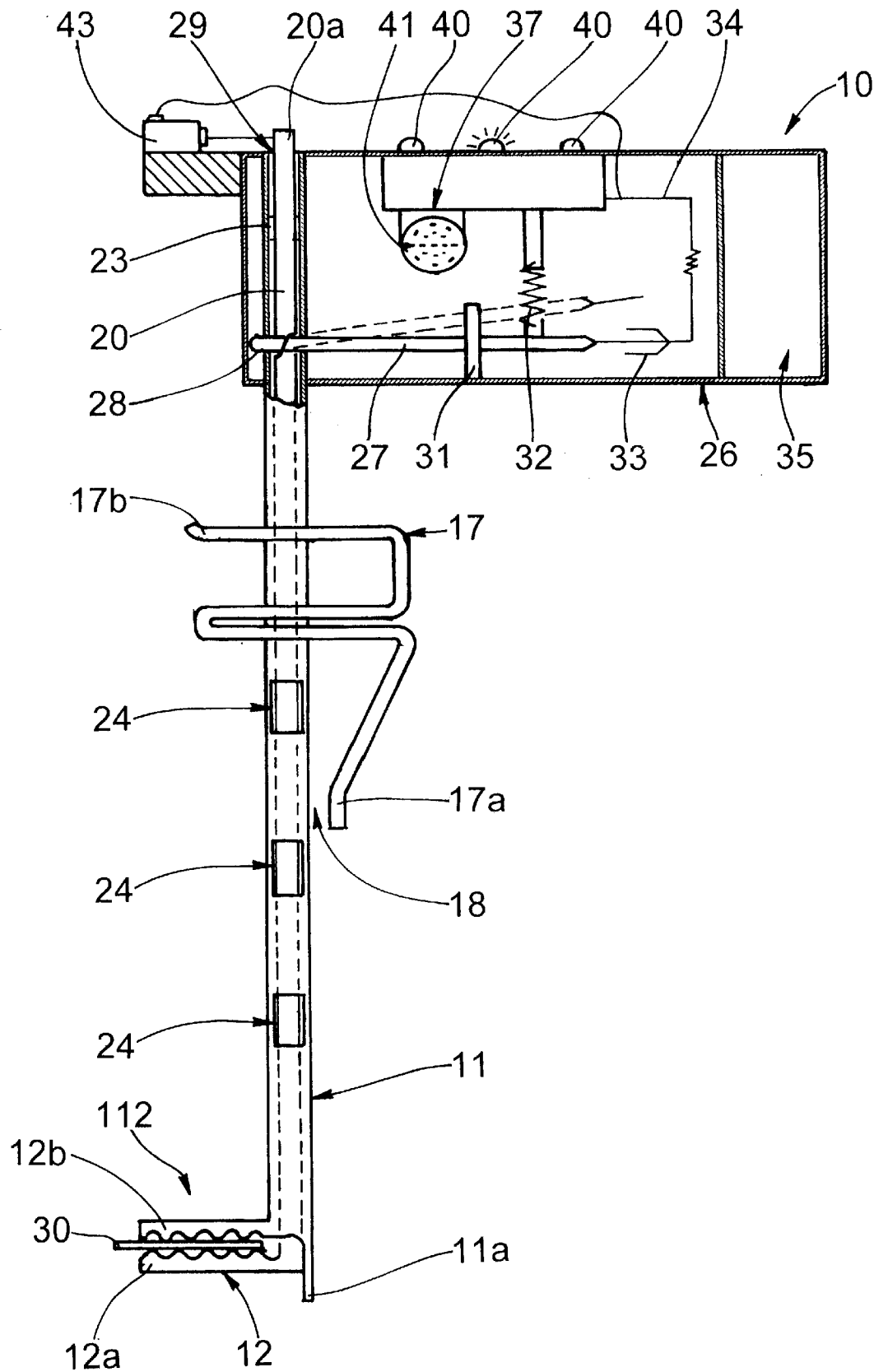
FIG. 2 shows a variant of FIG. 1.

In the embodiment shown in FIG. 2, the attachment means 13 comprise a shaped lamina 17 associated with the supporting element 11 and including an elastic end segment 17a defining, in cooperation with the supporting element 11, a coupling gap 18 for the edge of the saucepan.

In this case the supporting element for the lid of the saucepan consists of the upper segment 17b of the shaped lamina 17.

The squeezer element 12 comprises a pincer-type clamping device with upper 12b and lower 12a clamping elements.

At least one clamping element 12a or 12b is movable and is associated with a monitoring rod 20, whereas the other clamping element 12b or 12a is substantially stationary and is associated to the supporting element 11.

In the embodiment shown in FIG. 2, the upper element 12b is solid with the supporting element 11, whereas the lower element 12a is solid with the monitoring rod 20, which is mounted to slide on its axis inside the supporting element 11, and is guided by sliding elements 23.

In this case, the supporting element 11 has lateral openings 24 which impede the formation of calcium and make it possible to carry out any necessary "de-furring" operations more easily.

The supporting element 11 has a supporting extension 11a at the lower part which allows the squeezer element 12 to be held in a raised position with respect to the bottom of the saucepan.

In the embodiment shown in FIG. 1, the clamping elements 12a, 12b, where the upper element 12b is associated with the monitoring rod 20 while the lower element 12a is associated with the supporting element 11, are constrained together in an oscillating manner by means of an intermediate pin 21; there are spring means 19 cooperating with the rear end of the upper clamping element 12b.

The monitoring rod 20 in this case slides parallel to and outside the supporting element 11 and is guided by eyelets 22 solid with the supporting element 11.

The supporting element 11 is associated at the upper part with a box-like body 26 containing the selection commands 36 of the instrument 10 according to the invention and the elements 37 which signal that the pasta has reached the desired stage of cooking.

The upper segment of the monitoring rod 20 develops inside the box-like body 26, and protrudes at the upper part through a hole 29.

Inside the box-like body 26 the monitoring rod 20 is associated with a horizontally pivoting element 27.

In the embodiment shown in FIG. 2, the pivoting element 27 also cooperates with a guiding and containing profile 31 and is associated with a spring 32 fixed to the box-like body 26.

The pivoting element 27, according to the axial position of the monitoring rod 20, cooperates at the end with a plurality of contacts 33 aligned parallel to the monitoring rod 20 and connected to an electrical circuit 34, in this case fed by a battery housed in the seating 35 provided.

Each of the contacts 33 is paired with a defined stage of cooking of the pasta which can be pre-selected by means of the selection commands 36 on the outside casing of the box-like body 26.

The electrical circuit 34 is connected to the signal elements 37 which are activated according to the positioning of the pivoting element on the contact 33 which is selected and therefore activated.

Figure 3:
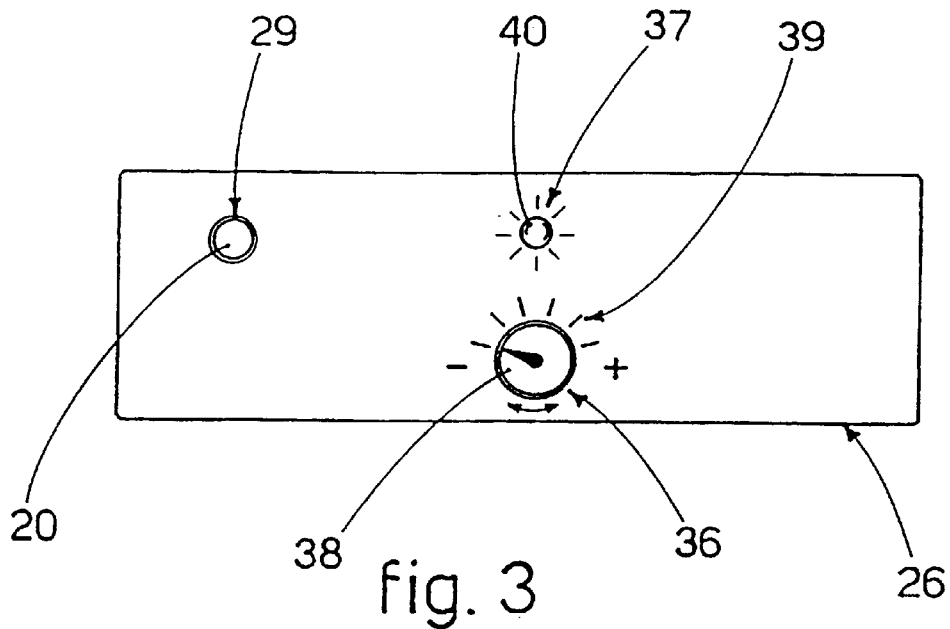
FIG. 3 shows a view from above of FIG. 1.

In the embodiment shown in FIGS. 1 and 3, the selection command 36 consists of a commutator 38 which can be arranged in six different positions 39, each of which is paired with a relative contact 33.

The instrument 10 comprises, in this case, a visual signal element 37 consisting of a led 40 and an audio signal element 37 consisting of a buzzer 41.

Figure 4:
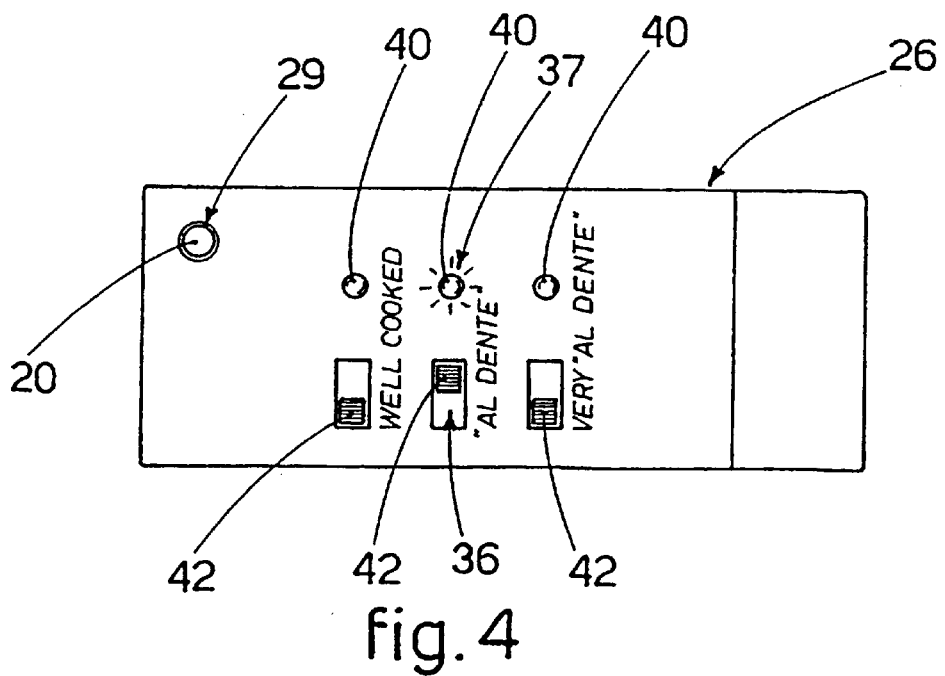
FIG. 4 shows a view from above of FIG. 2.

In the embodiment shown in FIGS. 2 and 4, the instrument 10 comprises three distinct selection commands consisting of switches 42 associated with relative contacts 33 and indicating a defined stage of cooking of the pasta.

Each switch 42 is associated with a relative led 40 which can be activated at the same time as a buzzer 41.

To use the instrument 10, the supporting element 11 must be introduced into the saucepan and the gripper means 112 immersed into the cooking liquid at the same time as the pasta is put into the saucepan when the water has reached boiling point.

First, the sample of pasta 30 is inserted between the clamping elements 12a and 12b.

The desired stage of cooking of the pasta ("al dente", very "al dente", well cooked.) is pre-set by means of the selection commands 36 which connect the circuit 34 to a defined contact 33.

In the case shown in FIG. 2, the monitoring rod 20 has fork means 28 solid thereto; when the rod 20 is pressed by pushing its upper end 20a which protrudes through the hole 29, the fork means 28 allow the movable lower clamping element 12a to move away from the stationary upper clamping element 12b until there is sufficient space to insert the sample of pasta 30.

At the same time, the fork means 28 take the pivoting element 27 into the start position, indicated by a line of dashes in the figure, compressing the spring means 32.

As the pasta cooks, it becomes less hard and consistent; this causes a progressive squeezing of the sample of pasta 30 by the lower clamping element 12a, under the action of the spring 32 which, thrusting against the pivoting element 27, maintains the monitoring rod 20, and therefore the lower clamping element 12a, elastically under tension.

As the sample of pasta 30 is squeezed, it causes a progressive movement of the lower clamping element 12a, which is solid with the monitoring rod 20 and therefore transmits thereto a gradual and mating upwards thrust.

The upwards movement of the monitoring rod 20 causes the progressive oscillation of the pivoting element 27 until it is arranged in correspondence with the contact 33 connected to the circuit 34.

In this position, the pivoting element 27 causes the circuit 34 to close and therefore the signal elements 37 associated thereto to be activated so as to advise the user that the pasta has reached the desired stage of cooking.

In the embodiment shown in FIG. 1, the spring 19 holds the upper clamping element 12b in elastic compression on the lower clamping element 12a; as cooking progresses, and therefore as the sample of pasta 30 loses its hardness and consistency, the upper clamping element 12b progressively gets closer to the lower clamping element 12a, with oscillation around the pin 21, and therefore the monitoring rod 20 attached to the rear part of the upper clamping element 12b is moved upwards.

This upwards movement of the monitoring rod 20 causes the pivoting element 27 to oscillate around the pin 43 and therefore the selected contact 33 is closed.

According to a variant which is not shown here, the closing of the circuit 34 causes the activation, or also the activation, of means to turn off the heating element under the saucepan.

According to another variant, the spring 19 or 32 can be gauged in a variable manner, so that it is possible to modify the sensitivity of the instrument 10 and personalise the degree of cooking which it signals.

According to yet another variant, the instrument 10 is associated with a basket to drain the pasta which can be removed from the saucepan.

According to another form of embodiment, the command from the squeezer element 12 to the circuit 34 is given electrically; this embodiment includes sensor means 43 associated with the clamping elements 12a and 12b, or with the monitoring rod 20, so as to monitor the position thereof, the sensor means being connected to the signal means.

According to a variant, the sensor means comprise a displacement transducer of the electric type, for example inductive, capacitive or resistive, or of the optical type.

What is claimed is:

1. An instrument for measuring the stage of cooking of pasta in a cooking liquid, the instrument comprising:

a gripper (112) immersed in the cooking liquid, the gripper including a squeezer (12) to retain and elastically compress a sample of the pasta (30), the squeezer (12) comprising a stationary contrasting element and an elastic compression element which includes elastic means with a fixed setting, the elastic compression element being movable with respect to the stationary contrasting element in a manner functionally correlated to the progressive loss of consistency of the sample of the pasta (30) as cooking proceeds, an electrical circuit (34) having at least one contact (33) and a signal (37), the position of the contact (33) being correlated to a predetermined state of cooking of the pasta;

a monitoring rod (20) attached to the elastic compression element and emerging from the cooking container;

a pivoting element attached to the monitoring rod (20) and cooperating electrically with the at least one contact (33) to close the electrical circuit (34) in response to movement of the monitoring rod (20) as the cooking of the sample of the pasta (30) proceeds to the predetermined state of cooking of the pasta (30), thereby activating the signal (37).

2. The instrument as in claim 1, further comprising a sensor to monitor the displacement of the monitoring rod (20), the sensor being electrically connected to the signal (37).

3. The instrument as in claim 1, wherein the signal (37) is of the luminous type (40).

4. The instrument as in claim 1, wherein the signal (37) is of the audio type (40).

5. The instrument as in claim 1, wherein the electrical circuit (34) includes a plurality of spaced apart contacts (33), each contact (33) being correlated with a different predetermined state of cooking of the pasta (30), the instrument further including a selection command (36) to select one of the contacts (33) such that when the pivoting element cooperates electrically with the selected contact (33) the electrical circuit (34) is closed.

6. The instrument as in claim 1, further comprising a body (26) containing at least the electrical circuit (34), the instrument further including a support (11) attached to the body (26) and to the gripper (112), and an attachment (13) movably mounted on the support (11) for attachment to the cooking container.

7. The instrument as in claim 6, wherein the attachment (13) includes an elastic fin (14), the instrument further including a screw (15) to attach the elastic fin (14) to the support (11).

8. The instrument as in claim 6, wherein the attachment (13) includes a shaped lamina (17) having an elastic segment (17a) defining a coupling gap (18) between the support (11) and elastic segment (17a).

9. The instrument as in claim 1, wherein the cooking liquid is contained in a cooking container with a lid, the instrument further comprising means (17b, 25a) to support the lid of the cooking container.

10. The instrument as in claim 1, wherein the support 11 includes openings (24) to impede the formation of calcium.

* * * * *